United States Patent
Moran et al.

(10) Patent No.: US 10,744,499 B2
(45) Date of Patent: Aug. 18, 2020

(54) SAMPLE HOLDER FOR ANALYSIS OF SOLID BIOLOGICAL SAMPLES

(71) Applicant: GE Healthcare UK Limited, Buckinghamshire (GB)

(72) Inventors: Nina Moran, Cardiff (GB); Michael John Smith, Cardiff (GB); Geraint Seymour, Cardiff (GB); Samantha Jane Ogden, Cardiff (GB); Leonard Goren, Piscataway, NJ (US)

(73) Assignee: GE Healthcare UK Limited, Buckinghamshire (GB)

( * ) Notice: Subject to any disclaimer, the term of this patent is extended or adjusted under 35 U.S.C. 154(b) by 44 days.

(21) Appl. No.: 14/888,225

(22) PCT Filed: Apr. 17, 2014

(86) PCT No.: PCT/EP2014/057926
§ 371 (c)(1),
(2) Date: Oct. 30, 2015

(87) PCT Pub. No.: WO2014/177397
PCT Pub. Date: Nov. 6, 2014

(65) Prior Publication Data
US 2016/0074859 A1    Mar. 17, 2016

(30) Foreign Application Priority Data
Apr. 30, 2013    (GB) .................... 1307762.3

(51) Int. Cl.
*B01L 9/00*        (2006.01)
*B01L 3/00*        (2006.01)
(Continued)

(52) U.S. Cl.
CPC ............. *B01L 3/502* (2013.01); *B01L 3/5029* (2013.01); *C12N 15/1017* (2013.01);
(Continued)

(58) Field of Classification Search
CPC .................... B01L 2300/0609; B01L 3/50825
(Continued)

(56) References Cited

U.S. PATENT DOCUMENTS 4,136,796 A * 1/1979 Dubois .............. B65D 51/1616
                                                220/259.4
4,396,583 A * 8/1983 LeBoeuf .............. A45C 11/005
                                                134/901
(Continued)

FOREIGN PATENT DOCUMENTS

EP        0 581 022 A1    2/1994
EP        0715858 A1      6/1996
(Continued)

OTHER PUBLICATIONS

GB Search Report issued in connection with GB application No. GB1307762.3 dated Nov. 1, 2013.
(Continued)

*Primary Examiner* — Natalia Levkovich
(74) *Attorney, Agent, or Firm* — Eversheds Sutherland (US) LLP

(57) ABSTRACT

A biological sample holder for holding a solid phase sample, including a handle, and a seal area suitable for being received in an opening of a sample receiving chamber of a cassette, mountable to a sample analysis instrument. The holder further includes a stem connected to the seal and a sample retainer connected to the stem for retaining solids in the retainer, the sample retainer including a perforated wall region for allowing fluids to pass through the wall but preventing the solid phase sample from passing through the wall.

6 Claims, 4 Drawing Sheets

(51) Int. Cl.
*C12N 15/10* (2006.01)
*C12Q 1/6806* (2018.01)
*A61B 10/00* (2006.01)
*G01N 1/40* (2006.01)

(52) U.S. Cl.
CPC ............ *C12Q 1/6806* (2013.01); *A61B 10/00* (2013.01); *B01L 2200/027* (2013.01); *B01L 2200/0631* (2013.01); *B01L 2300/047* (2013.01); *B01L 2300/0609* (2013.01); *G01N 1/4055* (2013.01)

(58) Field of Classification Search
USPC ........................................ 422/561, 560, 568
See application file for complete search history.

(56) References Cited

U.S. PATENT DOCUMENTS

| | | | |
|---|---|---|---|
| 4,439,319 A | 3/1984 | Rock | |
| 4,637,919 A * | 1/1987 | Ryder | A61L 12/128 220/371 |
| 5,558,846 A | 9/1996 | Alvord | |
| 6,899,850 B2 | 5/2005 | Haywood et al. | |
| 8,278,091 B2 | 10/2012 | Rutter et al. | |
| 9,012,208 B2 | 4/2015 | Selden et al. | |
| 9,108,193 B2 | 8/2015 | Feiglin | |
| 2003/0086830 A1 * | 5/2003 | Haywood | B01L 3/502 422/547 |
| 2007/0249961 A1 | 10/2007 | Morrison | |
| 2009/0100944 A1 | 4/2009 | Newby | |
| 2009/0104692 A1 * | 4/2009 | Bartfeld | A61B 10/0096 435/325 |
| 2011/0195495 A1 | 8/2011 | Seldon | |
| 2013/0065245 A1 | 3/2013 | Rutter | |

FOREIGN PATENT DOCUMENTS

| | | |
|---|---|---|
| JP | 2006242928 A | 9/2006 |
| WO | 2003031065 A1 | 4/2003 |
| WO | 2011094745 A2 | 11/2011 |

OTHER PUBLICATIONS

International Search Report issued in connection with corresponding WO application PCT/EP2014/057926 dated Apr. 30, 2013.
Office Action issued in connection with corresponding EP Application No. 14719701.6 dated Jan. 27, 2017.

* cited by examiner

SAMPLE HOLDER FOR ANALYSIS OF SOLID BIOLOGICAL SAMPLES

BACKGROUND

Embodiments of the present invention relate to methods and apparatus for processing of biological material in an automated or semi-automated analysis instrument.

It is known to provide automated instruments for analysis of biological samples. For example human identification by deoxyribonucleic acid (DNA) analysis can be performed using a commercially available instrument sold by GE Healthcare and NetBio Inc, under the trade name DNAscan.

That instrument uses a microfluidic system to wash a cotton tipped swab head (like a cotton bud) attached to a plastic stem which is in turn attached to a plastic cap. The swab is dimensioned such that it fits in a sample receiving chamber in the microfluidic circuit and the plastic cap holds the swab head in place suspended above the bottom of the chamber on the stem in the circuit. The position in which the swab head is held is important because the head must not block the microfluidic circuit, but fluids in the circuit must be allowed immerse the head and reach the whole of the head to optimise the chances of collecting any sample material held on the head. The instrument is automatic, meaning that it processes the eluted sample by means of fluidic hardware and software without intervention. Other instruments are semi-automatic, meaning that some intervention may be required, but the principal analysis steps are carried out without intervention by hardware and software.

This known arrangement of sample swab is satisfactory for liquid phase biological samples that are capable of being transferred onto a cotton swab, but biological samples which may contain DNA are often only available in a solid phase form, e.g. dry, or in a form which cannot easily be transferred to a cotton swab. For example: fabrics; cigarette butts; chewing gum; body tissue; hair; and nail clippings could all contain DNA which could be recovered if the DNA were transferable onto a cotton swab, but that transfer is not guaranteed simply by wiping the cotton swab over the surface of those materials. Other such materials are readily apparent to a skilled addressee.

Where the sample cannot be transferred onto a swab, or where the transfer is not certain, then some other way is required to provide a sample to known microfluidic instruments which will not interfere with the operation of the instrument, but which can be collected easily, and held in the instrument at the correct position.

Embodiments of the present invention address the above problems.

SUMMARY OF THE INVENTION

According to a first aspect, the invention provides, a biological sample holder for holding a solid phase sample, including, at a proximal end, a handle and seal area suitable for being received in or around an opening of a sample receiving chamber of a sample analysis instrument, the holder further including a stem portion connected to the seal area, being narrower in width than the seal area, and a sample retainer connected to the stem at a distal end of the holder for retaining solids in or adjacent the retainer, the sample retainer including a perforated wall region for allowing fluids to pass through the wall but preventing the solid phase sample from passing through the wall.

According to a second aspect, the invention provides a biological sample receiving cassette adapted for fitting to a fluidic circuit of a sample analysis instrument, the cassette including a receiving chamber having at least one fluidic circuit port, and an opening for receiving a biological sample holder, the apparatus further including a sample holder, having, at a proximal end, a handle and seal area suitable for being received in or around the opening, the holder further including a stem portion connected to the seal area, being narrower in width than the seal area, and a sample retainer connected to the stem at a distal end of the holder for retaining solids in or adjacent the retainer, the sample retainer including a perforated wall region for allowing fluids to pass through the wall but preventing the solid phase sample from passing through the wall.

According to a third aspect the invention provides a method for processing a solid phase biological sample in an analysis instrument, for analysis of nucleic acids and/or proteins, the method comprising the steps of: providing a sample holder including at a proximal end, a handle and seal area, the holder further including a stem portion connected to the seal area, being narrower in width than the seal area, and a sample retainer connected to the stem at a distal end of the holder for retaining a solid phase sample in the retainer, the sample retainer including a perforated wall region for allowing fluids to pass through the wall but preventing solids from passing through the wall; providing a biological sample receiving cassette adapted for fitting to a fluidic circuit of an automated or semi-automated sample analysis instrument, the cassette including a receiving chamber having at least one fluidic circuit port, and an opening for receiving the biological sample holder; inserting the holder in the chamber, immersing the retainer in fluid from the fluid circuit, and processing the fluid in order to obtain the nucleic acids or proteins.

Embodiments and features of the present invention are defined by the dependent claims herein.

BRIEF DESCRIPTION OF THE DRAWINGS

The invention can be put into effect in numerous ways. By way of example, embodiments are described below, with typical examples being illustrated in the drawings, wherein.

DETAILED DESCRIPTION

Figure 1:
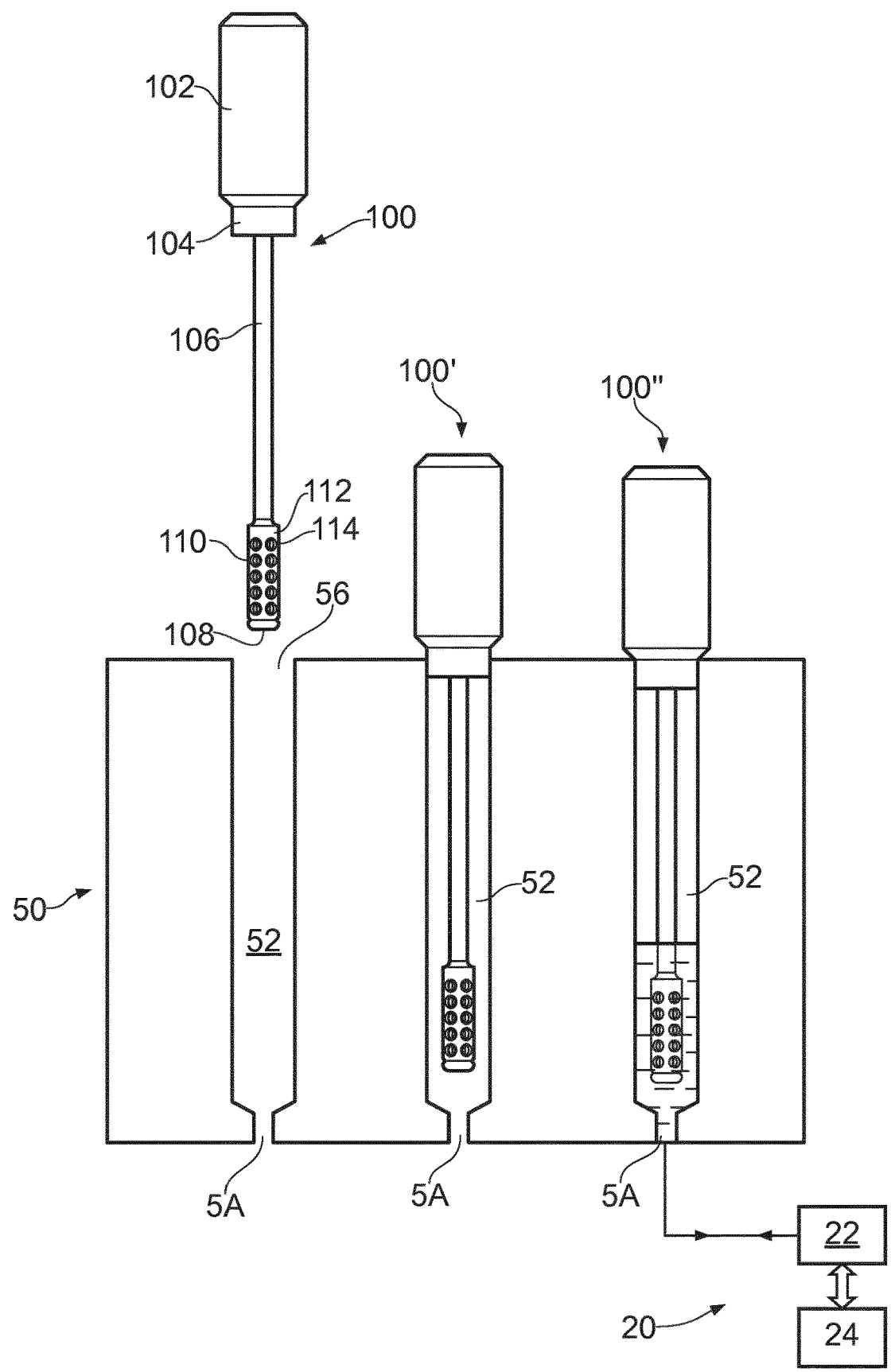
FIG. 1 shows a first sample holder in different positions relative to a sample cassette, during use.

Referring to FIG. 1 there is shown a sample holder 100, a sample holder receiving cassette 50 and, schematically, an analysis instrument 20.

The sample holder comprises a handle 102 which has a sealing cap region 104, a narrowed stem 106 connected to the handle at the sealing cap, and a sample retainer 110 connected to the stem at a distal end thereof. The sample retainer is a cage having a cage wall 112 defining a region within which is captured a biological sample in use. The biological sample, which may include any of the material identified above, but is not limited to those materials, is placed directly into the sample cage. The sample is inserted into the cage by means of removing an end plug 108, to access the cage. The plug 108 can be refitted, in this case with a resilient snap fit to retain the sample. Perforations 114 provide fluid communication into the cage, but prevent the sample from leaving the cage.

In use the sample holder is fitted into the cassette 50 as shown by the position of sample holder 100' in FIG. 1. The cassette has receiving chambers 52. For convenience three chambers 52 are shown, but it is equally likely that just one, two, or more chambers could be employed. In this position, the sealing cap 104 engages a complementary surface of the chamber to hermetically seal the receiving chamber 52. Also the cap acts to support the stem and cage and suspend the same in the chamber to provide correct positioning of the cage in the chamber.

The cassette 50 is assembled with an analysis instrument 20, which includes a fluidic circuit 22, connected to the chamber 52 by an inlet/outlet port 54, and connected to controlling hardware/ software 24. The inlet/outlet port 54 allows liquid reagents/air to enter and exit the chamber 52 to enable DNA extraction according to known biochemical techniques. A resulting eluted sample solution is directed out through the port for further processing by the fluidic circuit 22 under the control of hardware and software 24, again according to known techniques. In summary, these techniques include an extraction process comprising the introduction to the sample chamber of a first reagent solution (lysis buffer), delivered via the port followed by ethanol and chaotic bubbling to mix the reagents and effect cell lysis. The DNA is transferred from the sample substrate into the liquid solution. The solution is then taken out of the chamber through the port where it is then passed through a silica membrane. The DNA is bound to this membrane and the remaining liquid is delivered back into the sample chamber which now acts as a holder for waste liquid reagents. The DNA bound to the membrane is then washed and eluted off into solution for amplification and subsequent separation & detection.

The perforations 114 are dimensioned to allow the liquid processing reagents to enter in and out of the cage freely to make contact with the sample, but do not allow the sample to escape, thus preventing the sample from falling down and blocking the port 54 or from floating above the liquid level. In practice, it has been found that circular perforations of about 1 mm work well, but smaller perforations are adequate and other shapes suffice, provided that they are numerous enough to allow liquid flow, but do not allow the solid sample to escape. The cage is dimensioned also to allow the sample to move freely within the solution to allow good DNA extraction. A minimum dimension (most likely the internal diameter of cylindrical cage) of between 2 mm and 6 mm is considered to provide sufficient freedom of movement of a small sample and sufficient volume for free fluidic movement of the reagents employed. For example a 3 mm disk punched from a collection paper sold by Whatman Inc under the brand name FTA could be placed in the cage of 4 mm and have sufficient clearance to move freely.

FIGS. 2,3 and 4 show further embodiments of a sample holder, but the process for extracting biological information from samples they hold is substantially the same as described above.

Figure 2A:
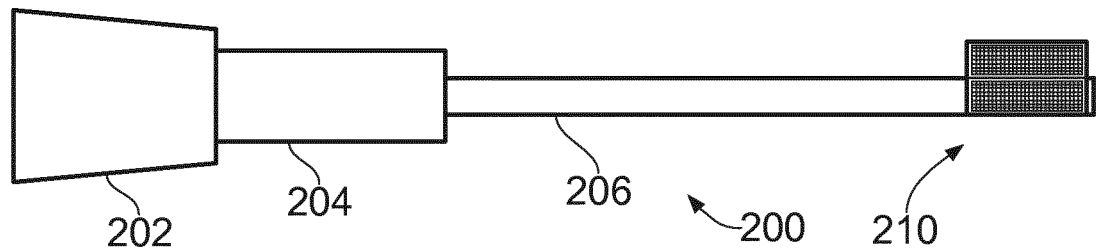
FIGS. 2A, 2B and 2C show a second sample holder.
Figures 2B, 2C:
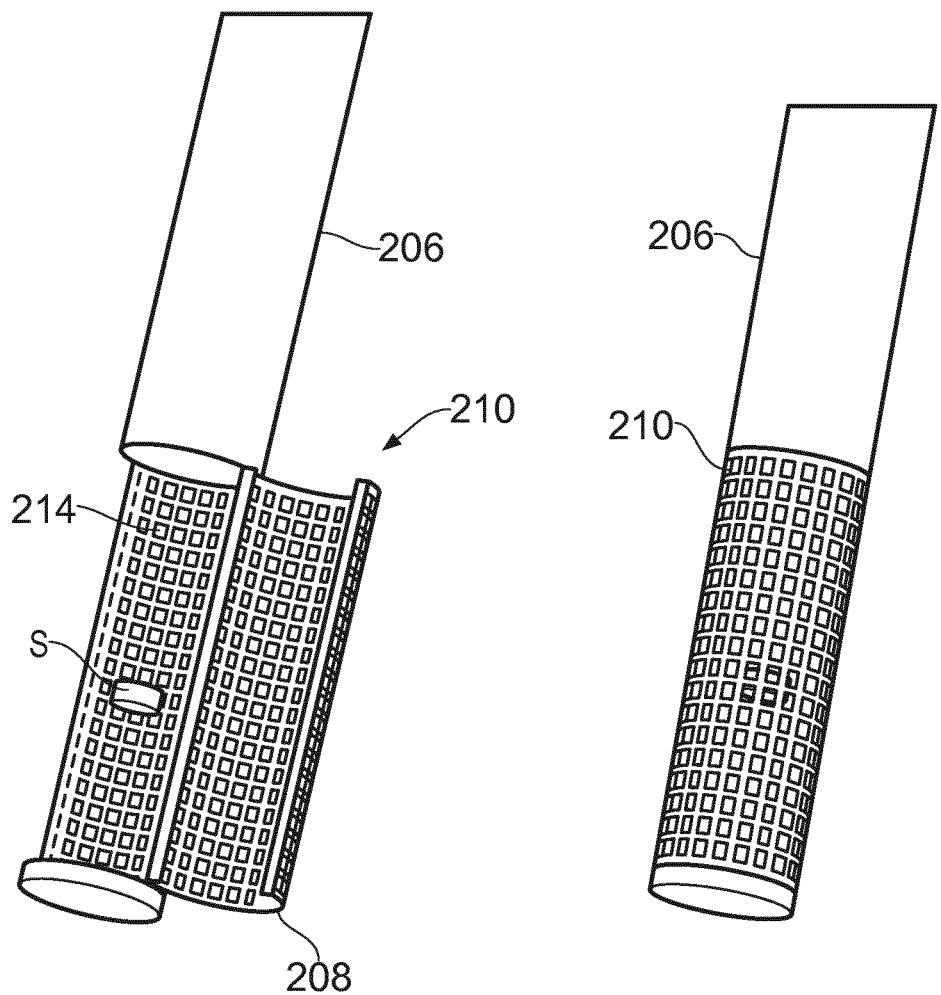
Figure 3A:
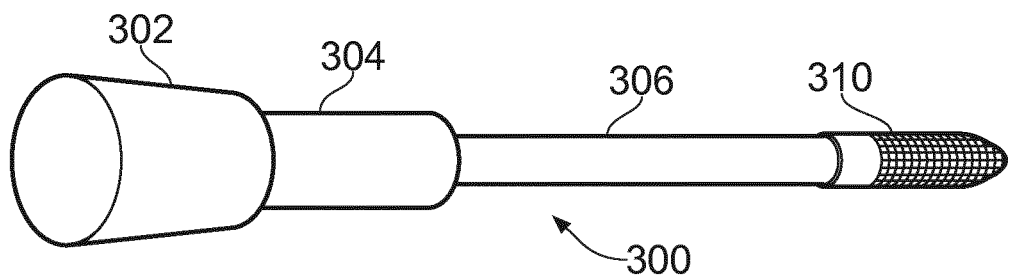
FIGS. 3A, 3B, 3C and 3D shows a third sample holder.
Figures 3C, 3D:
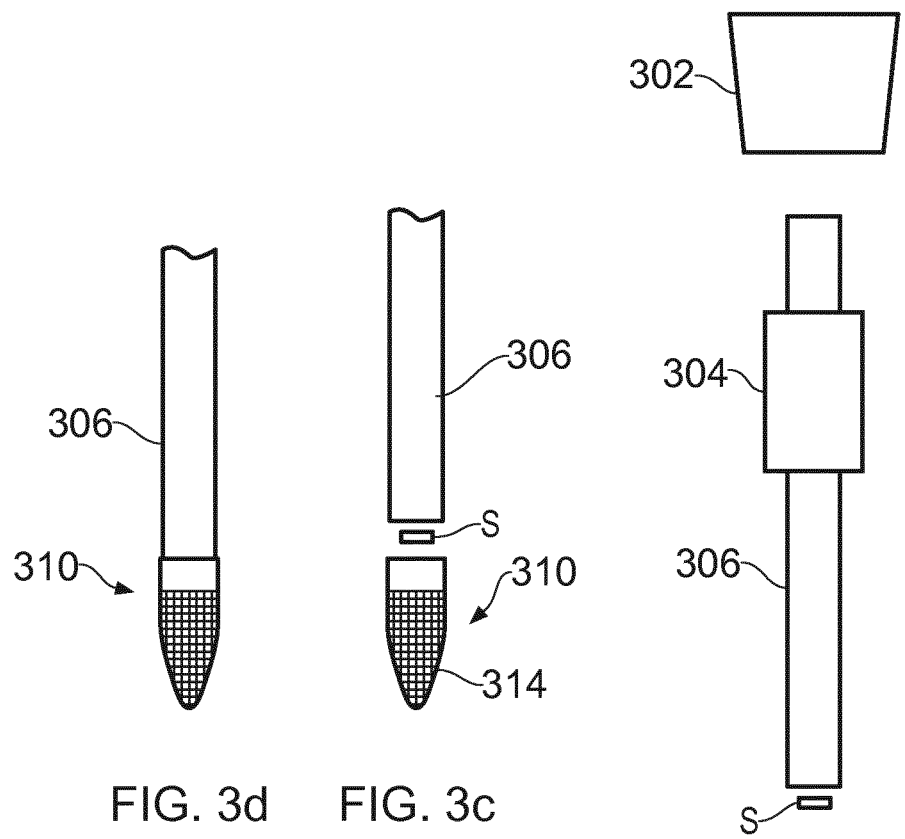

Referring to FIG. 2a, an alternative sample holder 200 is shown. This embodiment includes a handle 202, which has a sealing cap region 204, a narrowed stem 206 connected to the handle at the sealing cap, and a sample retainer 210 connect to the stem at the distal end of the stem. Referring additional to FIGS. 2b, and 2c which show enlarge views of the retainer 210, the sample retainer 210 is a cage having a cage wall 212 defining a region within which is captured a biological sample S in use, and a door 208 for closing the cage. The biological sample S, which may include any of the material identified above, but is not limited to those materials, is placed directly into the sample cage 210. The door 208 of the cage is closed (as shown in FIG. 2c), and the door is held shut by means of frictional engagement within the remainder of the cage. Perforations 214 in the cage and its door 208 provide fluid communication into the cage, but prevent the sample from leaving the cage.

Referring to FIGS. 3a, 3b, 3c and 3d, a further alternative sample holder 300 is shown. Elements in the embodiment shown in FIGS. 3a, 3b, 3c and 3d which are equivalent to the elements of the embodiments shown in FIGS. 1 and 2 are referenced with the same last two digits.

In FIGS. 3a, 3b, 3c and 3d, the retainer is in the form of a cup 310 fitted to the end of a stem 306. A sample S is placed in the cup before the cup is attached to the stem. The cup is perforated at its lower half, to allow fluid flow into and out of the retainer, for processing the sample as described above.

Figure 4A:
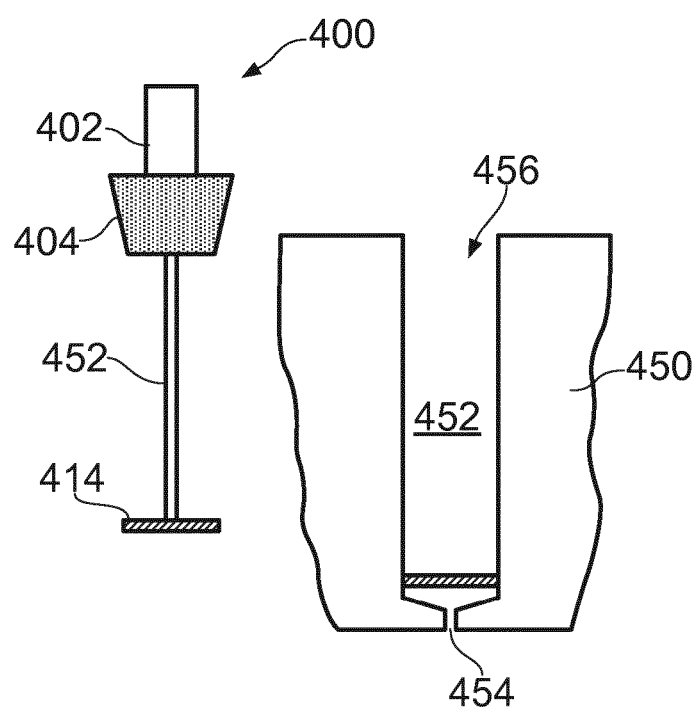
FIGS. 4A and 4B shows a forth sample holder.
Figure 4B:
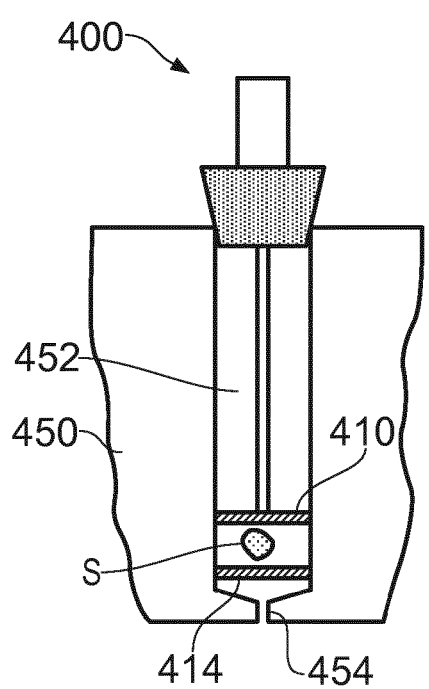

FIGS. 4a and 4b show another embodiment of a sample holder. Again elements in the embodiment shown which are equivalent to elements of previously described embodiments are referenced with the same last two digits.

In FIGS. 4a and 4b a sample holder 400 includes a perforated retainer disk 410 which in use is inserted the receiving chamber 452 of a cassette 450 on top of a sample S to hold down the sample. The disk 410 allows fluid to pass. The disk has a peripheral shape which is substantially the same shape as the inner wall of the chamber. A further perforated element 414 is fitted into the base of the chamber 452, between the opening 456 of the chamber and the fluid port 454, to stop the sample S from clogging the port. Again the element 414 is substantially the same size as the chamber. In use the retainer 410 and the element 414 allow fluid to flow, for processing the sample S according to the above mentioned techniques.

The volume defined by the retainer 410 and the element 414 and their respective perforations allow the reagents to flow effectively around the sample S for efficient processing. The solution containing the DNA exits through the port 454 outlet channel for downstream processing as described previously, and the remaining sample substrate is retained inside the sample chamber between the two meshes.

Although only four embodiments of a sample holder have been described and illustrated, it will be apparent to the skilled addressee that modifications, variants, additions and omissions are possible within the scope and spirit of the invention defined herein.

For example, in the embodiment shown in FIG. 1, the plug 108 is said to be resiliently snap fitted to the cage 110, however other methods for attaching that plug are possible, for example a screw thread, or self-locking taper, such as a Luer Lock® could be used. The same alternatives could be used to hold the cup 310 in place on the stem 306.

The terms 'perforations', or 'perforated' are intended to encompass both fine holes or pores which can allow liquid phase materials to pass (including DNA strands in suspension in a liquid), and larger holes (up to 3 or 4 mm) which prevent large objects (e.g. fabric, or chewing gum) hosting biological samples from escaping.

Figure 3B:
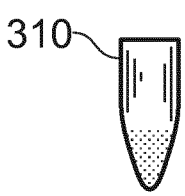

In an embodiment, the materials used for the sample holders shown are plastics, for example polypropylene. Moulded plastics offer advantages, of low cost manufacture. The door 208 and the remaining retainer 210 could be manufactured as one moulding, along with the stem 206, for low cost. Rather than single mouldings, individual components could be used, for example as shown in FIG. 3b. This allows different materials to be employed, for example where lower quality plastics could be employed for the handle 302, and/or where a more resilient material is needed for the sealing cap 304, to provide a good seal.

Although the invention has been described with reference to its use for recovering DNA, it is equally applicable to the recovery of ribonucleic acids (RNA) and proteins, from solid phase samples.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A biological sample holder for holding a solid phase sample, comprising:
    a handle having a proximal end and a distal end,
    a sealing cap region having a proximal end and a distal end, wherein the proximal end of the sealing cap region is connected to the distal end of the handle, wherein the sealing cap region is suitable for being sealably received in or around an opening of a sample receiving chamber of a sample analysis instrument,
    a stem portion having a proximal end and a distal end, wherein the proximal end of the stem portion is connected to the distal end of the sealing cap region, the stem portion being narrower in width than the handle or sealing cap region, and
    a sample retainer having a proximal end and a distal end, wherein the proximal end of the sample retainer is connected to the distal end of the stem portion, wherein said sample retainer further comprises a perforated wall region allowing liquids and soluble reagents to pass through the perforated wall region and preventing a solid phase sample in the sample retainer from passing through the wall region.

2. A biological sample holder as claimed in claim 1, wherein the perforated wall region further comprises a. door which is openable for inserting or removing the sample and is closable to keep the sample in the sample retainer.

3. A biological sample holder as claimed in claim 2, wherein the door further comprises a. hinge attached to the sample holder for opening and closing the door.

4. A method for processing a solid phase biological sample in an analysis instrument, for analysis of nucleic acids and/or proteins, said method comprising the steps of:
    providing a sample holder of claim 1;
    providing a biological sample receiving cassette adapted for fitting to a fluidic circuit of an automated or semi-automated sample analysis instrument, the cassette including a receiving chamber having at least one fluidic circuit port, and an opening for receiving the biological sample holder; and,
    inserting the holder in the chamber, immersing the sample retainer in fluid from the fluid circuit, and processing said fluid in order to obtain said nucleic acids or proteins.

5. A biological sample holder as claimed in claim 1, wherein the sample retainer includes an access for allowing insertion of the sample and is closable to keep the sample in the retainer, wherein the access comprises an opening blockable by the stem, wherein the stem and the opening are configured for fittingly attaching to each other.

6. The biological sample holder as claimed in claim 5, wherein the perforated wall region of the sample retainer is a cage.

* * * * *